(12) United States Patent
Oguma

(10) Patent No.: US 6,353,755 B1
(45) Date of Patent: Mar. 5, 2002

(54) MEASURING APPARATUS WHICH FACILITATES ALTERATION OF STORED VARIABLES IN MEASURING A CERTAIN CHARACTERISTIC OF AN OBJECT, AND APPLICATIONS OF SUCH MEASURING APPARATUS TO MEASUREMENTS OF HEALTHY INDICIA AND BODY FAT PERCENTAGE

(75) Inventor: Koji Oguma, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/663,930

(22) Filed: Sep. 18, 2000

(30) Foreign Application Priority Data

Sep. 22, 1999 (JP) .......................................... 11-268229
Jul. 10, 2000 (JP) .......................................... 12-208882

(51) Int. Cl.$^7$ ................................................. A61B 5/00
(52) U.S. Cl. ..................................................... 600/547
(58) Field of Search ................................. 600/547, 587, 600/300

(56) References Cited

U.S. PATENT DOCUMENTS 5,579,782 A    12/1996   Masuo

FOREIGN PATENT DOCUMENTS

JP            5-2164        1/1993
JP          10-174679        6/1998

OTHER PUBLICATIONS

European Search Report.

*Primary Examiner*—Max Hindenburg
(74) *Attorney, Agent, or Firm*—McDermott, Will & Emery

(57) ABSTRACT

Disclosed is an improvement in a measuring apparatus comprising: an inputting device including an inputting-and-setting switch for inputting and recording a plurality of pieces of information, data-modifying switches for changing a selected one or ones of the plurality of pieces of information and a measurement starting switch for starting measurement of a certain characteristic of an object; a measuring device for measuring the certain characteristic of the object; a memory device for storing the plurality of pieces of information inputted by the inputting device; an arithmetic and control unit (ACU) for determining a required indicia from the certain characteristic of the object and from the plurality of pieces of information; and a display for showing the plurality of pieces of information and the so determined indicia. The arithmetic and control unit is responsive to depression of the data-modifying switches subsequent to depression of the measurement starting switch for putting the measuring apparatus in its inputting state, thereby permitting alteration of a selected one of the plurality of pieces of information. Renewal of often changeable variables selected among those stored in the memory is permitted without the necessity of repeating the inputting and recording of the other data. Such exclusive renewal improves significantly the operability of such measuring apparatus.

14 Claims, 14 Drawing Sheets

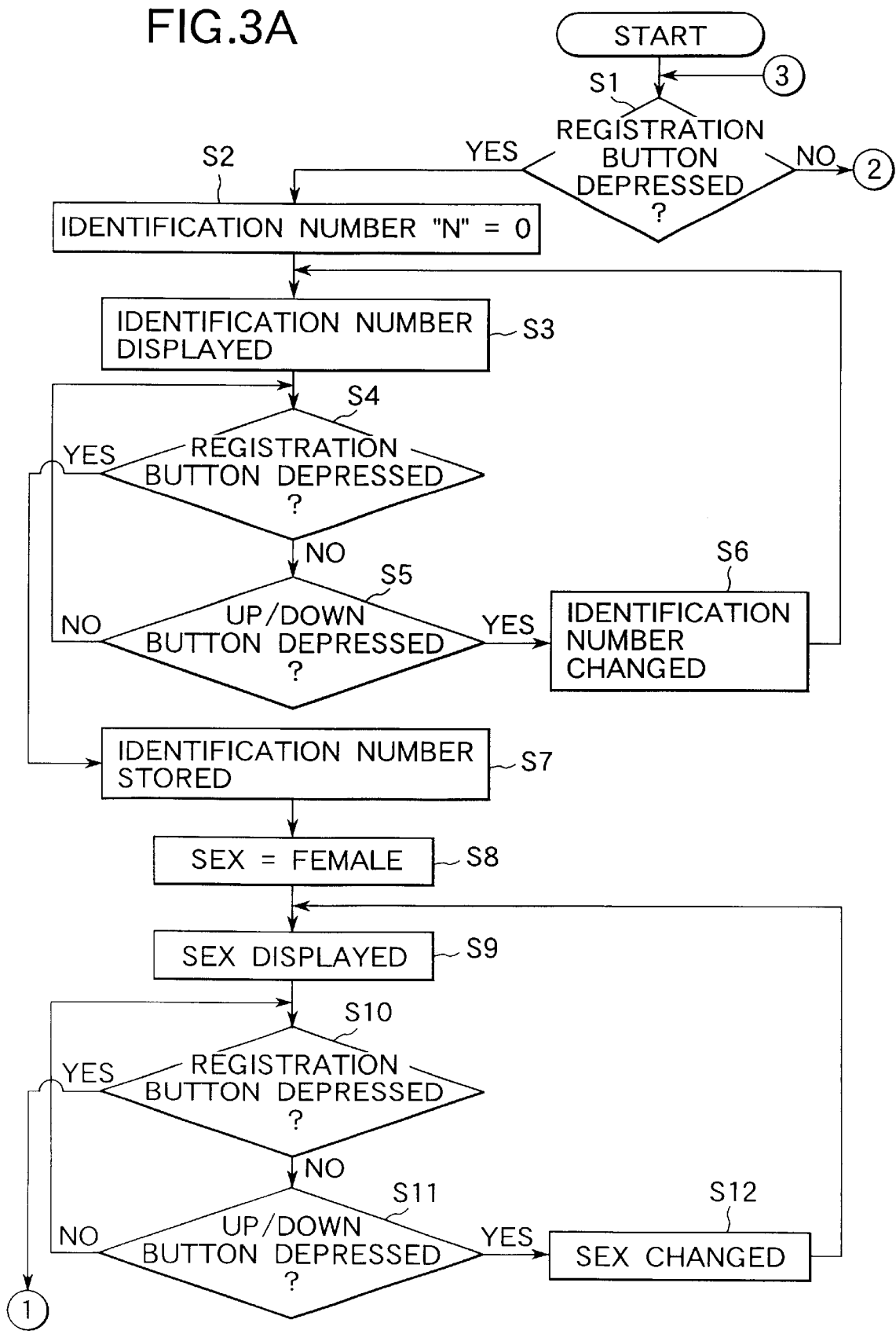

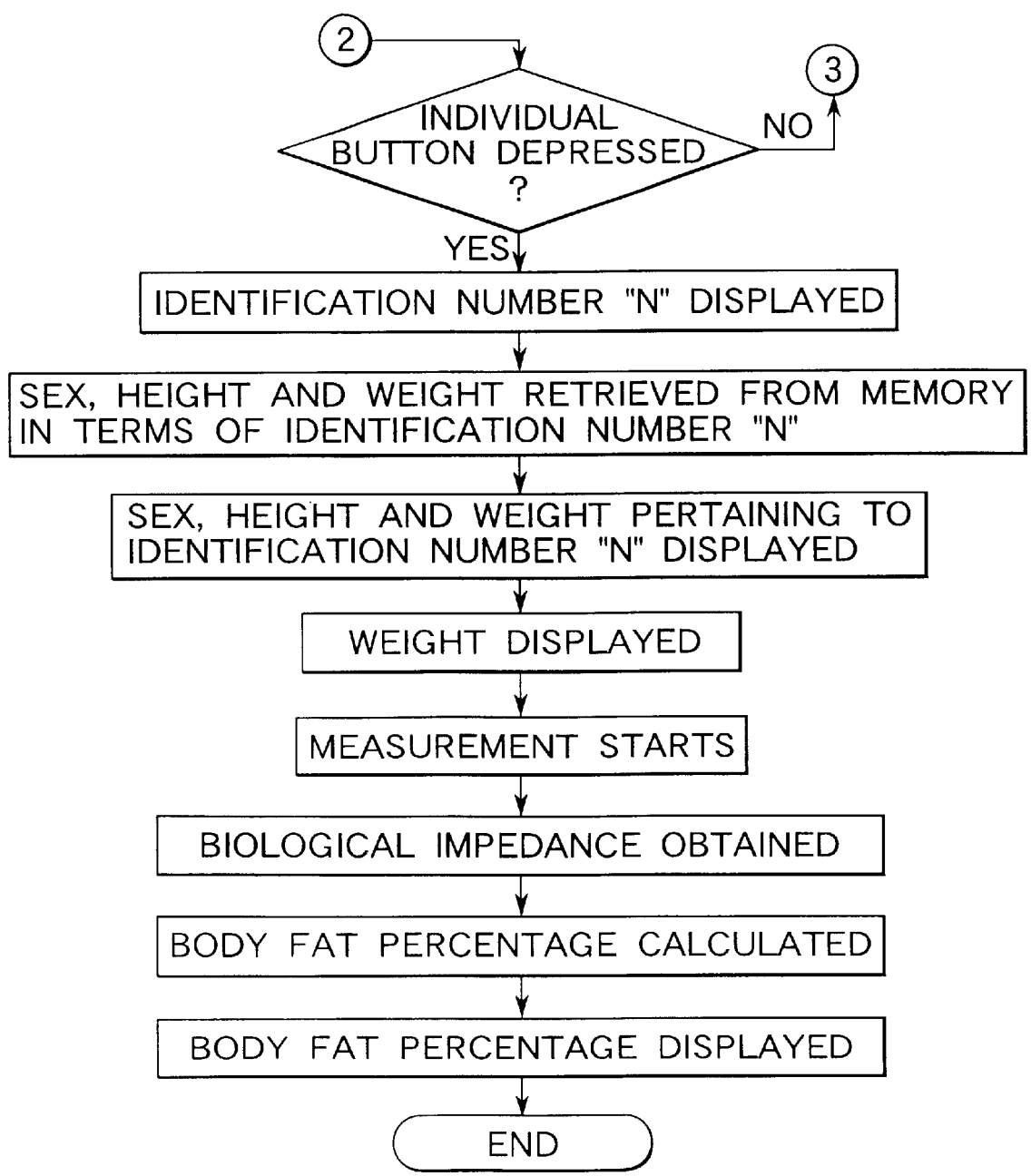

MEASURING APPARATUS WHICH FACILITATES ALTERATION OF STORED VARIABLES IN MEASURING A CERTAIN CHARACTERISTIC OF AN OBJECT, AND APPLICATIONS OF SUCH MEASURING APPARATUS TO MEASUREMENTS OF HEALTHY INDICIA AND BODY FAT PERCENTAGE

FIELD OF THE INVENTION

The present invention relates to a measuring apparatus whose arithmetic and control unit can determine a certain characteristic of an object from a plurality of pieces of information inputted. Examples of such measuring apparatus are a healthy indicia measuring apparatus and a body fat percentage gauge.

PRIOR ART

Japanese Utility Model Application Laid-Open No.5-2164 shows a card-like body fat percentage gauge having a display and a console on its front side and four measurement electrodes on its rear side. Two measurement electrodes are arranged on its left side whereas the remaining two measurement electrodes are arranged on its right side. Thus, two fingers of either hand can be put on these electrodes when one's body fat percentage is being measured. A pocket-sized body fat percentage gauge commercially available from NAMCO Ltd., has one electrode each on its front and rear sides. Another pocket-sized body fat percentage gauge commercially available from Yamato Scale Co. Ltd., has two electrodes on the upper part each of its front and rear sides.

These gauges determine the body fat percentage on the basis of the biological impedance of an individual while he or she holds the gauge with his or her hands putting on paired electrodes, thereby permitting the biological impedance appearing between the selected points of hands to be determined. Body fat is likely to impede the flow of electric current greately compared with muscle, blood and lymph, which conduct electric current well. Therefore, the body fat percentage can be determined in terms of impedance. Calculation of the body fat percentage in terms of the biological impedance must take physical variables of the individual into account, and therefore, the sex, height, weight and other variables are inputted in the body fat percentage gauge prior to measurement. As a matter of fact, some extra pieces of physical information such as human races, athletes, adults or children and ages are inputted in the body fat percentage gauge.

If the body fat percentage gauge should require the inputting of such variables every time a required measurement is made, the gauge is inconvenient. In the hope of reducing such inconvenience the gauge is equipped with memories for storing such variables once inputted in the gauge, and an individual can have an access to his or her particulars simply by inputting his or her identification number.

Referring to FIG. 5, a series of actions taken by the prior art gauge follow in measuring the body fat percentage are shown in the form of flow chart. The series of actions on the left side pertain to registration of the physical variables of an individual whereas those on the right side pertain to the measurement of the body fat percentage. As seen from the left part of the flow chart, the identification number, the sex, the height and the weight are stored in the order named in the memory.

Usually the body fat percentage gauge is used while an individual is limiting the amount and type of food that the individual eats in order to become thinner or while an individual continues to take good exercise in order to strengthen his muscle, and therefore, the weight varies significantly in a relatively short length of time. A weight scale type of body fat percentage gauge permits automatic measurement of the weight simultaneous with measurement of the body fat percentage, thus making it unnecessary to input the instantaneous or present weight. The hand-holding type of body fat percentage gauge requires the reentering of all variables, that is, the identification number, the sex, the height and finally the weight, preventing the changing of the sole variable of weight, which can be inputted after having inputted all the preceding variables as seen from the left part of FIG. 5. Apparently this is inconvenient in using the body fat percentage gauge.

SUMMARY OF THE INVENTION

One object of the present invention is to provide a measuring apparatus which facilitates alteration of selected variables in measuring a certain characteristic of an object.

Another object of the present invention is to provide application of such measuring apparatus to measurement of healthy indicia.

Still another object of the present invention is to provide application of such measuring apparatus to measurement of body fat percentage.

To attain these objects a measuring apparatus comprising: an inputting device comprising;
  an inputting-and-setting switch for inputting and recording a plurality of pieces of information, data-modifying switches for changing a selected one or ones of the plurality of pieces of information and a measurement starting switch for starting measurement of a certain characteristic of an object;
  a measuring device for measuring the certain characteristic of the object;
  a memory device for storing the plurality of pieces of information inputted by the inputting device;
  an arithmetic and control unit (ACU) for determining a required indicia from the certain characteristic of the object and from the plurality of pieces of information; and
  a display for showing the plurality of pieces of information and the so determined indicia, is improved according to the present invention in that
  the arithmetic and control unit is responsive to depression of the data-modifying switches subsequent to depression of the measurement starting switch for putting the measuring apparatus in its inputting state, thereby permitting alteration of a selected one of the plurality of pieces of information.

The measuring apparatus may comprise a selector switch for selecting a desired piece of information for alteration among the selected ones of the plurality of pieces of information.

The arithmetic and control unit may be responsive to depression of the measurement starting switch for permitting the display device to show a registered piece of information for alteration in the display prior to and during the measurement of the certain characteristic of the object.

The arithmetic and control unit may be responsive to appearance of unusual values as representing the certain characteristic of the object for permitting the display device to continue to show the registered piece of information for alteration, for repeating determination of the certain characteristic of the object until the so determined characteristic of the object has been reduced to a normal value, and for obtaining the indicia from the normal value of the characteristic of the object finally determined and selected pieces of information retrieved from the memory, thereby permitting the display to show the required indicia.

A healthy indicia measuring apparatus comprising:

an inputting device comprising an inputting-and-setting switch for inputting and recording a plurality of pieces of physical information pertaining to each individual, data-modifying switches for changing a selected one or ones of the plurality of pieces of physical information and a measurement starting switch for starting measurement of a certain characteristic of each individual;

sensors for obtaining a selected piece or pieces of biological information;

a memory for storing the plurality of pieces of physical information pertaining to each individual inputted by the inputting device;

an arithmetic and control unit (ACU) for determining a healthy indicia from the stored pieces of physical information and from the measured piece of biological information; and a display for showing the pieces of physical information and the so determined healthy indicia, is improved according to the present invention in that the arithmetic and control unit is responsive to depression of the data-modifying switches subsequent to depression of the measurement starting switch for putting the healthy indicia measuring apparatus in its inputting state, thereby permitting alteration of a selected one of the stored pieces of physical information.

The healthy indicia measuring apparatus may further comprise a selector switch for selecting a desired piece of information among two or more selected ones of the stored pieces of physical information.

The arithmetic and control unit may be responsive to depression of the measurement starting switch for permitting the display device to show a given piece of physical information for alteration in the display prior to and during the measurement of the biological information.

The arithmetic and control unit may be responsive to appearance of unusual values as representing the measurement of the piece of biological information for permitting the display device to continue to show the registered piece of physical information for alteration, for repeating determination of the biological information of the individual until the so determined biological information has been reduced to a normal value, and for obtaining the healthy indicia from the normal value of the so determined biological information and selected pieces of physical information retrieved from the memory, thus permitting the display to show the required healthy indicia.

A body fat percentage measuring apparatus comprising:

an inputting device comprising an inputting-and-setting switch for inputting and recording a plurality of pieces of physical information pertaining to each individual, data-modifying switches for changing the sex, the age, the height, the weight and other pieces of physical information of each individual, and a measurement starting switch for starting the measurement of the body fat percentage for each individual;

a biological impedance sensor having electrodes to be applied to the individual body;

a memory for storing the pieces of physical information pertaining to each individual inputted by the inputting device;

an arithmetic and control unit (ACU) for determining the body fat percentage from the determined biological impedance and from the stored pieces of physical information; and a display for showing the pieces of physical information and the so determined body fat percentage, is improved according to the present invention in that the arithmetic and control unit is responsive to depression of the data-modifying switches subsequent to depression of the measurement starting switch for putting the body fat percentage measuring apparatus in its inputting state, thereby permitting alteration of a selected one of the stored pieces of physical information pertaining to each individual.

The body fat percentage measuring apparatus may further comprise a selector switch for selecting a desired piece of information among two or more selected ones of the pieces of physical information.

The arithmetic and control unit may be responsive to depression of the measurement starting switch for permitting the display device to show the registered piece of physical information for alteration in the display prior to and during the measurement of the biological impedance.

The arithmetic and control unit may be responsive to appearance of unusual values as representing the biological impedance for permitting the display device to continue to show the registered piece of information desired for alteration, for repeating determination of the biological impedance until the so determined biological impedance has been reduced to a normal value, and for obtaining the body fat percentage from the normal value of the biological impedance and selected pieces of information retrieved from the memory, thus permitting the display to show the required body fat percentage.

One piece of physical information to be selected for alteration may be weight.

The piece of physical information selected for alteration may be one of the weight and height selected by the selector switch.

Other objects and advantages of the present invention will be understood from the following description of preferred embodiments of the present invention, which are shown in accompanying drawings:

FIGS. 3A, 3B and 3C show a flowchart describing a series of actions taken by the hand-held type of body fat percentage gauge according to one embodiment of the present invention;

FIGS. 8A, 8B and 8C show a flowchart describing a series of actions taken by a conventional body fat rate percentage gauge.

DESCRIPTION OF PREFERRED EMBODIMENTS

Figure 1:
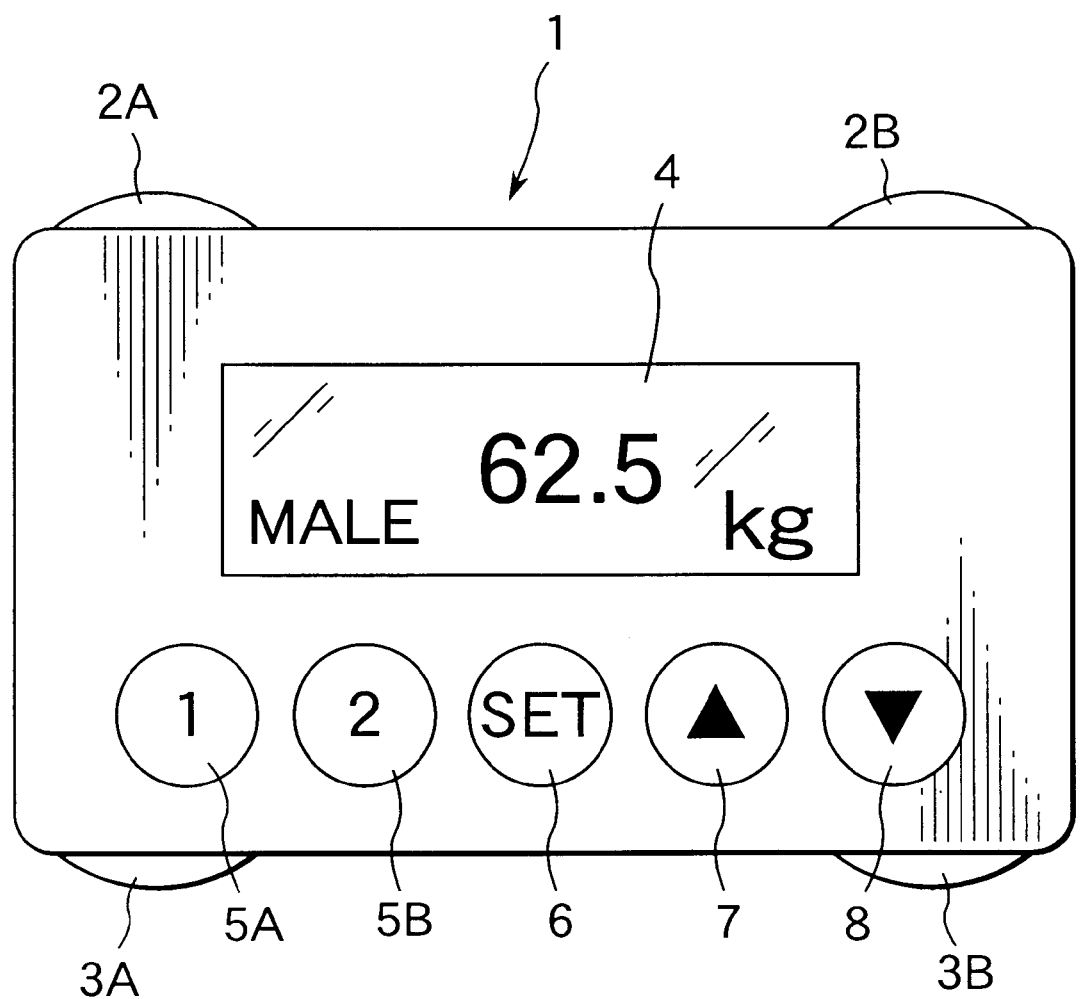
FIG. 1 shows a hand-held type of body fat percentage gauge to which the present invention is applied.

Referring to FIG. 1, a hand-held type of body fat percentage gauge 1 according to one preferred embodiment of the present invention has, on its upper and lower longitudinal sides and on its front surface, a pair of current supplying electrodes 2A and 2B, a pair of voltage measuring electrodes 3A and 3B, a display 4 for indicating a measured body fat percentage and pieces of physical information set for each individual, push buttons 5A and 5B for measurement, allotted to two individuals respectively, a push button 6 for registration, and up-scroll and down-scroll push buttons 7 and 8. The push buttons for measurement 5A and 5B can be used in inputting a selected identification number, retrieving the identification number and starting the measurement of body fat percentage. The push button 6 for registration can be used when it is desired that the gauge is put in the individual setting mode in which pieces of physical information pertaining to an individual can be inputted, and when a desired number is registered in place of the corresponding registered number. The up-scroll and down-scroll push buttons 7 and 8 can be used in changing the pieces of physical information pertaining to an individual, such as sex, height and weight. The current supplying electrodes 2A and 2B and voltage measuring electrodes 3A and 3B are biological impedance sensors, which are so arranged that: the thumb of the left hand may be put on the electrode 3A; the index finger of the left hand may be put on the electrode 2A; the thumb of the right hand may be put on the electrode 3B; and the index finger of the right hand may be put on the electrode 2B.

Figure 2:
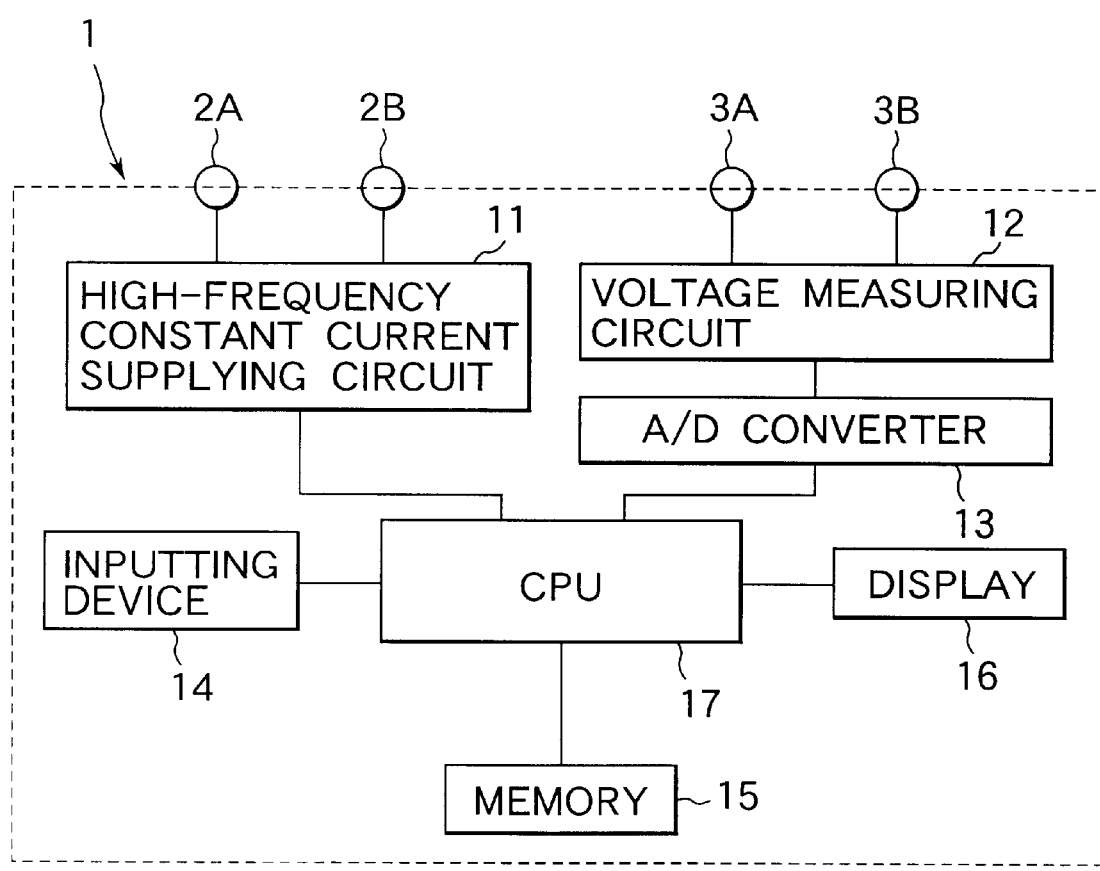
FIG. 2 is a block diagram of electric components of the hand-held type of body fat percentage gauge.

Referring to FIG. 2, the electric circuit arrangement of the hand-held type of body fat percentage gauge comprises a high-frequency constant current supplying circuit 11 for supplying the current supplying electrodes 2A and 2B with electric current, a voltage measuring circuit 12 for measuring the voltage appearing between the voltage measuring electrodes 3A and 3B, an analog-to-digital converter 13 for converting the measured voltage in digital form, an inputting device 14 comprising switches 5 to 8 for entering pieces of physical information for each individual and starting the measurement, a memory device 15 for storing the pieces of physical information pertaining to each individual, a display device 16 including the display 4 for indicating the pieces of physical information pertaining to each individual and the results of calculations, and an arithmetic and control unit (CPU) 17 for calculating a body fat percentage from the measured biological impedance and the pieces of physical information, and for permitting the display to indicate the result of the calculation and permitting the memory to store the same.

Figure 3B:
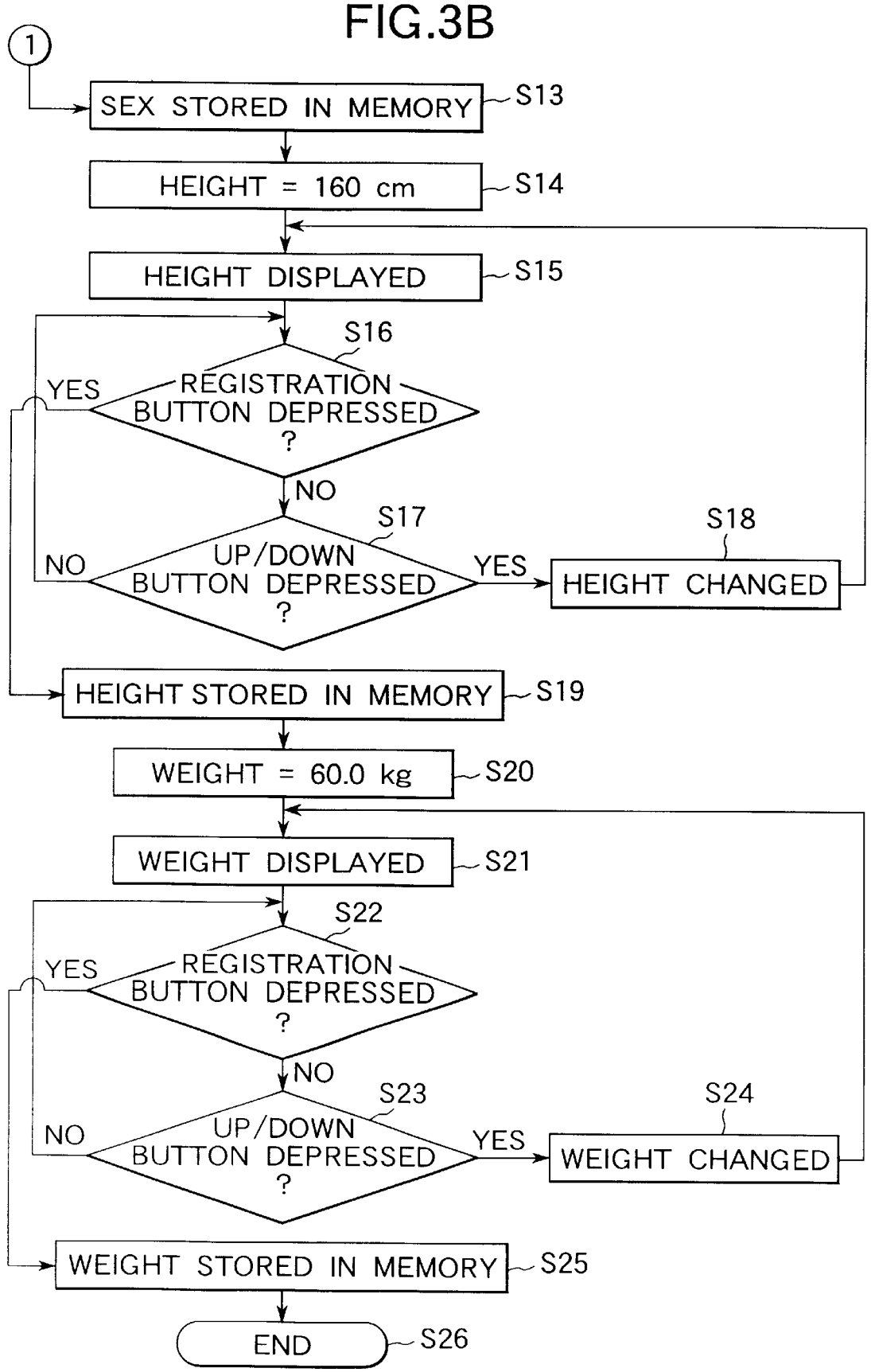
Figure 3C:
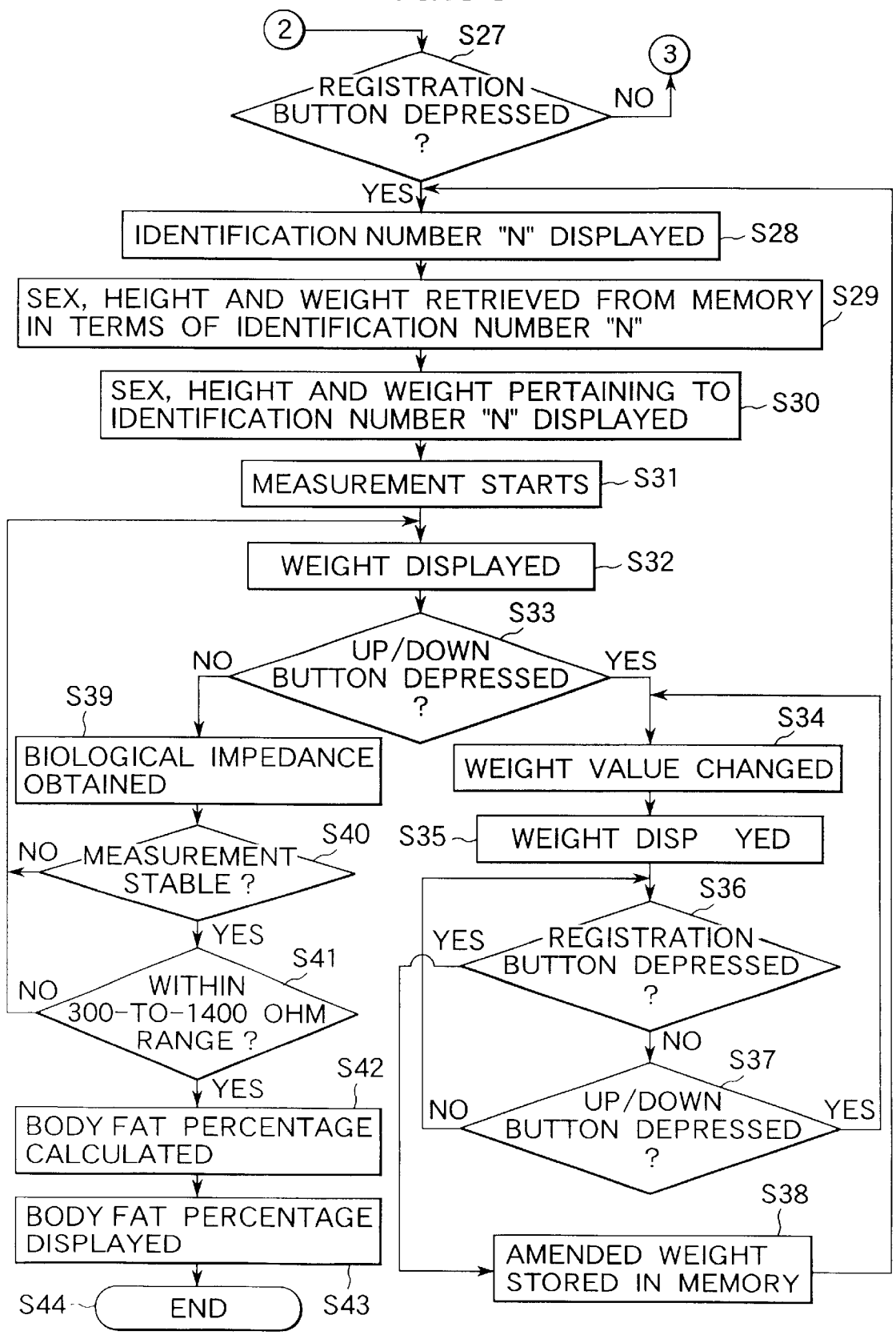

Referring to FIGS. 3A, 3B and 3C, a series of actions taken by the body fat percentage gauge when being set up (see FIGS. 3A and 3B), and another series of actions taken by the gauge when measuring the body fat percentage (see FIG. 3C) are described below: at first, the gauge is ready to work in response to depression of one of the individual measurement push buttons 5A and 5B and the registration push button 6, allowing the display, analog circuits, CPU and other circuit components to remain dormant, thus consuming no electric power. Depression of the registration push button 6 will put the gauge in the individual data setting mode. Otherwise, the gauge is still standing by (Step S1).

Depression of the registration push button 6 will set zero to an identification number "n" (Step S2), allowing the display 4 to show 0 as the initial value (Step S3). A check is made again as to whether or not the registration push button 6 has been depressed (Step S4). In the negative case a check is made as to whether or not either of the up- and down-scroll push button has been pushed (Step S5). In the affirmative case the identification number "n" is altered, and then, the proceeding returns to Step 3. (Step S6). If the registration push button 6 is found to have been depressed at Step 4, the number appearing in the display 4 is stored as the identification number in the memory (Step S7), which can store different pieces of physical information for each identification number.

Selection of the sex follows registration of the identification number, and "female" is set as an initial value (Step S8), allowing the display 4 to show the sex (Step S9). Then, a check is made as to whether or not the registration push button 6 has been depressed (Step S10). In the negative case a check is made as to whether or not either scroll button has been depressed (Step S11). In the affirmative case the indicated sex is changed, and then the proceeding returns to Step S9 (Step S12). If the registration push button 6 is found to have been depressed at Step S10, the sex appearing in the display 4 is stored in the memory (Step S13).

The entering of the height follows registration of the sex, and 160 cm is set to the height as an initial value (Step S14), allowing the display 4 to show the initial value (Step S15). Then, a check is made as to whether or not the registration push button 6 has been depressed (Step S16). In the negative case a check is made as to whether or not either scroll button has been depressed (Step S17). In the affirmative case the initial value is changed, and then the proceeding returns to Step S15 (Step S18). If the registration push button 6 is found to have been depressed at Step S16, the height appearing in the display 4 is stored in the memory (Step S19).

The entering of the weight follows registration of the height, and 60.0 kg is set to the weight as an initial value (Step S20), allowing the display 4 to show the initial value (Step S21). Then, a check is made as to whether or not the registration push button 6 has been depressed (Step S22). In the negative case a check is made as to whether or not either scroll button has been depressed (Step S23). In the affirmative case the initial value is changed, and then the proceeding returns to Step S21 (Step S24). If the registration push button 6 is found to have been depressed at Step S22, the weight appearing in the display 4 is stored in the memory (Step S25). Thus, all pieces of physical information pertaining to the individual are registered. Thus, the individual data setting mode is finished (Step S26).

If the registration push button 6 is not depressed at Step S1, a check is made as to whether or not either push button for measurement 5A or 5B has been depressed (Step S27). In the negative case the proceeding returns to Step S1. The body fat percentage gauge remains dormant until either measurement push button 5A or 5B has been depressed. Contrary, if the registration push button 6 is found to have been depressed at Step S27, the identification number "n" pertaining to the depressed measurement push button is allowed to appear in the display 4 (Step S28), so that the sex, the height and the weight of the individual thus identified in terms of identification number "n" are retrieved from the memory (Step S29). The so retrieved sex, height and weight are allowed to appear one after another in the display 4 (Step S30). Then, the body fat rate gauge 1 is put in the measurement-permitting condition (Step S31), allowing the display 4 to continue to show the value of weight retrieved from the memory at Step 29 (Step S32). This continuous display informs the user of the permissibility of changing the displayed value on demand.

Here, a check is made as to whether or not either scroll push button 7 or 8 has been depressed (Step S33). In the affirmative case the value of weight is amended (Step S34), and the amended value of weight is shown in the display 4 (Step S35). A check is made as to whether or not the registration push button 6 has been depressed (Step S36). Thus, the user is being asked whether the amended and displayed value is acceptable. In the negative case a check is made as to whether or not either scroll push button 7 or 8 has been depressed (Step S37). If either scroll push button 7 or 8 is depressed, the proceeding is allowed to return to Step S34 for renewal of the displayed value. If not, the proceeding is allowed to return to Step S36 to confirm that the weight has been corrected to the present value of weight, and that the amended value should be registered. Depression of the registration push button 6 at Step 36 allows the memory to store the amended value (Step S38), and then the preceding returns to Step S28.

If either scroll push button 7 or 8 is not depressed for renewal of values at Step 33, a biological impedance is calculated (Step S39). The calculation is repeated several times within a relatively short time, and a check is made as to whether or not the so determined values of biological impedance remain within a certain range (Step S40). If the so determined values of biological impedance are found to be unstable, increasing or decreasing beyond the certain range, the proceeding returns to Step S32. When the so determined values of biological impedance are found to be stable, it is checked whether these values remain within the range from 300 to 1,400 Ω (Step S41). The values of biological impedance appearing between both hands of children and adults remain in the range from 300 to 1,400 Ω. If the measurement is effected with both hand skins touched on the electrodes, the values of biological impedance must remain within the range. Stated otherwise, if the values of biological impedance are found to be out of the range, either hand skin is supposed to have been untouched rightly on the electrodes on which it must be put.

Figure 4:
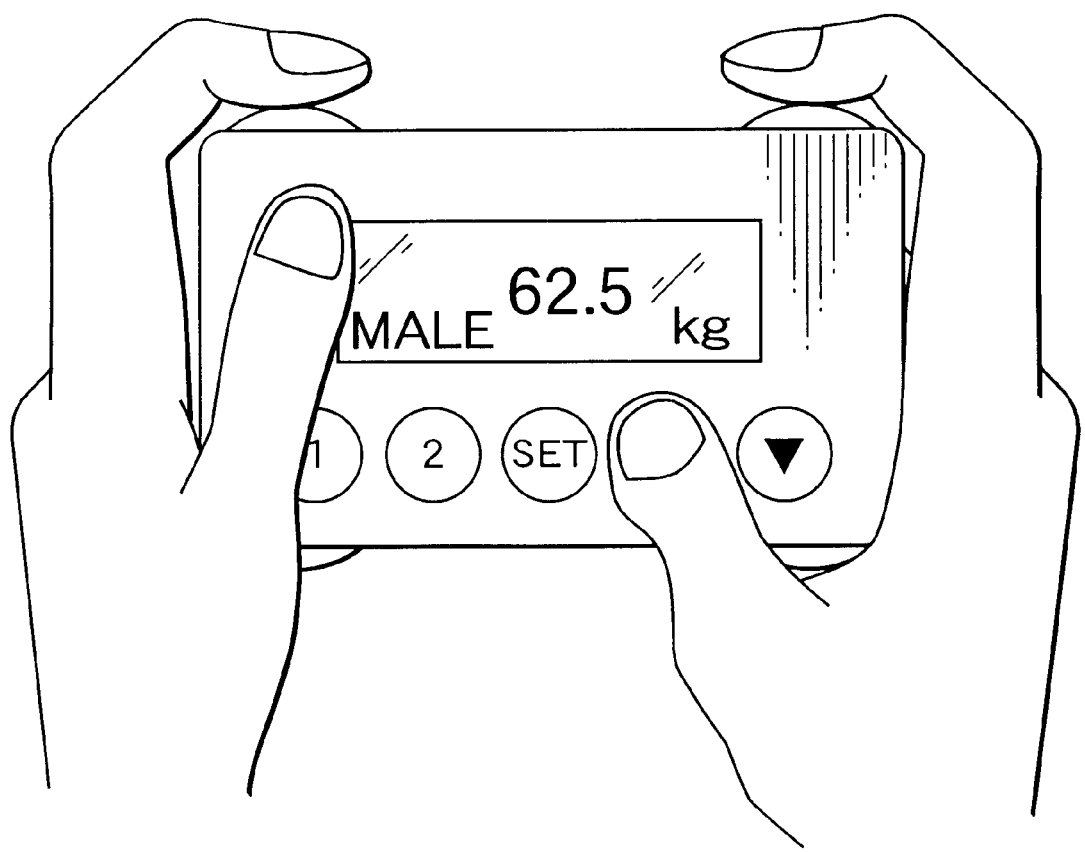
FIG. 4 illustrates how both hands are used in measuring the body fat percentage.

As seen from FIG. 4, the user uses his thumbs in changing some pieces of physical information already registered, and then, he must take at least one of both thumbs off from the voltage measuring electrode, resulting in the value of biological impedance departing apart from the prescribed range. Continuous measurement of biological impedance reveals that the user is changing the registered value of his weight, and then, the display device continues to show the registered value of weight. Thus, the user can compare the present weight with the registered one until the value of biological impedance has been stable in measurement. When the measured value of biological impedance is found to be stable at Step S40, and when the measured value is found to remain within the 300-to-1400 ohm range at Step S41, the user is supposed to put his fingers on the electrodes, indicating his desire for measurement of biological impedance. Thus, some words, such as "measurement continued" appear in the display 4.

The body fat percentage is calculated from the measured value of biological impedance and some pieces of physical information retrieved from the memory, such as the sex, the height and the (amended) weight (Step S42). The body fat percentage thus calculated is shown in the display 4 (Step S43), and it will disappear from the display 4 in a given length of time, thus completing all measurements (Step S44).

Figure 5:
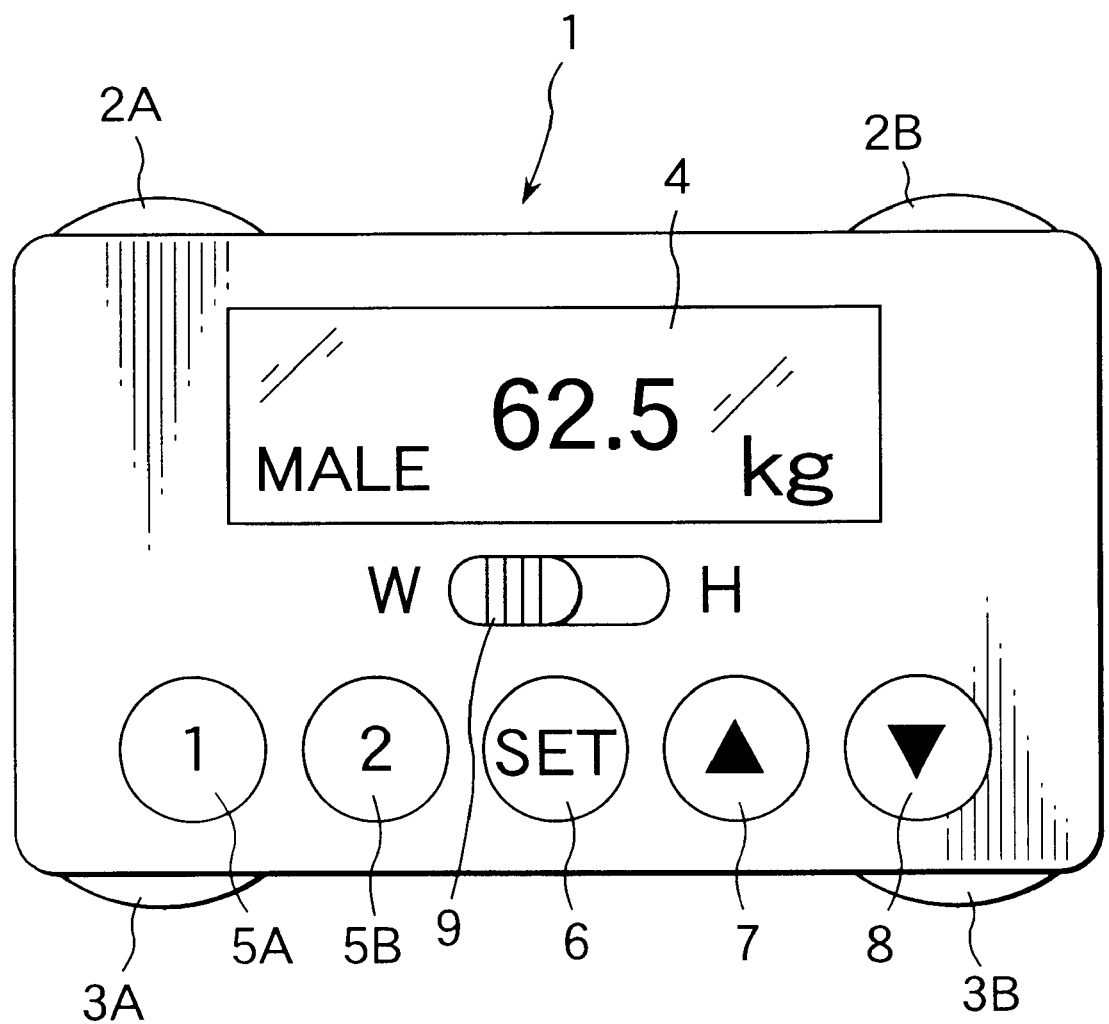
FIG. 5 shows a hand-held type of body fat percentage gauge which is modified according to the present invention.

Referring to FIG. 5, another hand-held type of body fat percentage gauge 1 which is modified according to the present invention has, on its front surface, a variable selector switch 9 in addition to those appearing in FIG. 1. The variable selector switch 9 can be used in selecting the piece of information to be changed while the gauge is standing by for measurement. Conveniently some pieces of information which are required often for renewal, such as weight or height can be readily selected for access.

Figure 6:
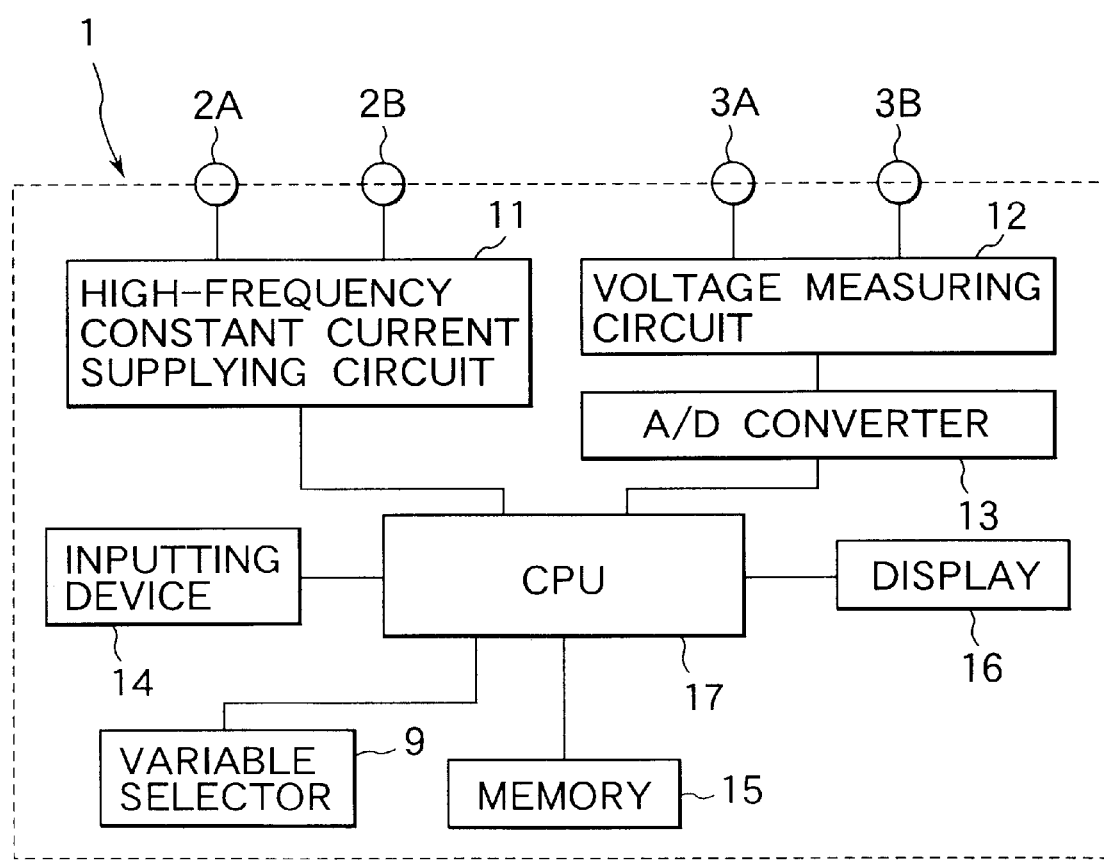
FIG. 6 is a block diagram of electric components of the hand-held type of body fat percentage gauge of FIG. 5.

Referring to FIG. 6, the electric circuit arrangement similar to that shown in FIG. 2 has such variable selector switch 9 connected to the arithmetic and control unit (CPU) 17.

Figure 7A:
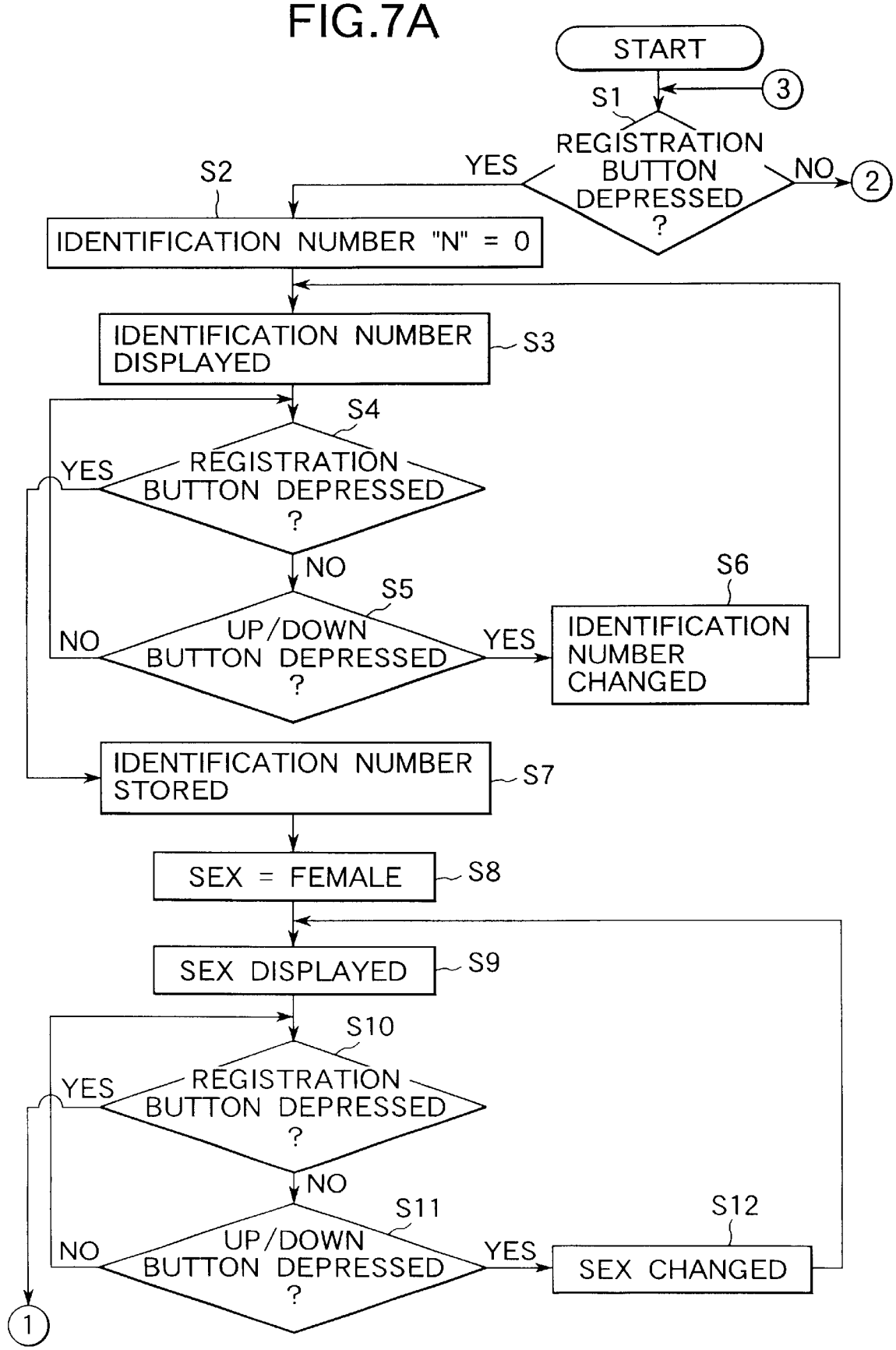
FIGS. 7A, 7B and 7C show a flowchart describing a series of actions taken by the hand-held type of body fat percentage gauge according to another embodiment of the present invention.
Figure 7B:
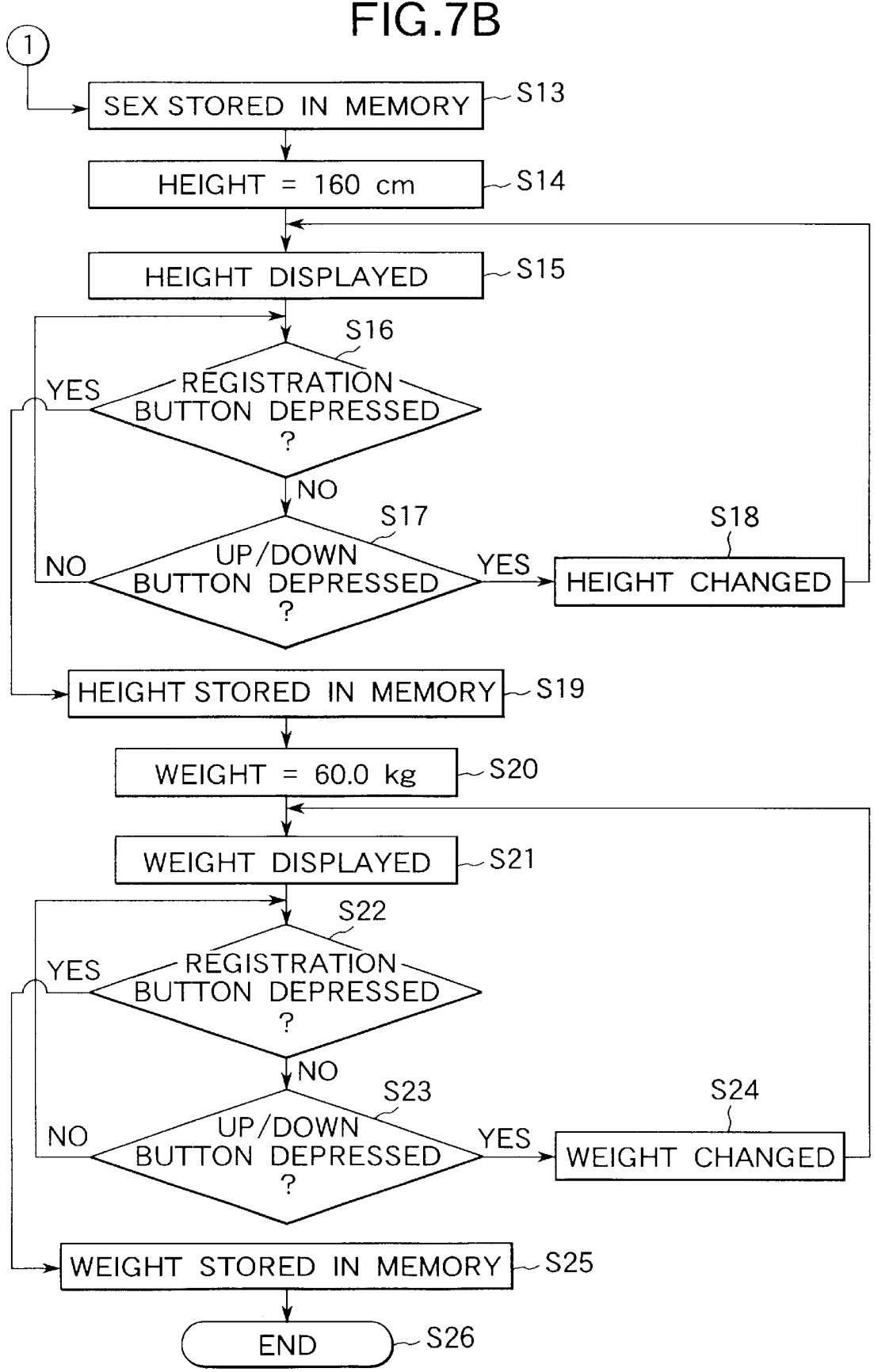
Figure 7C:
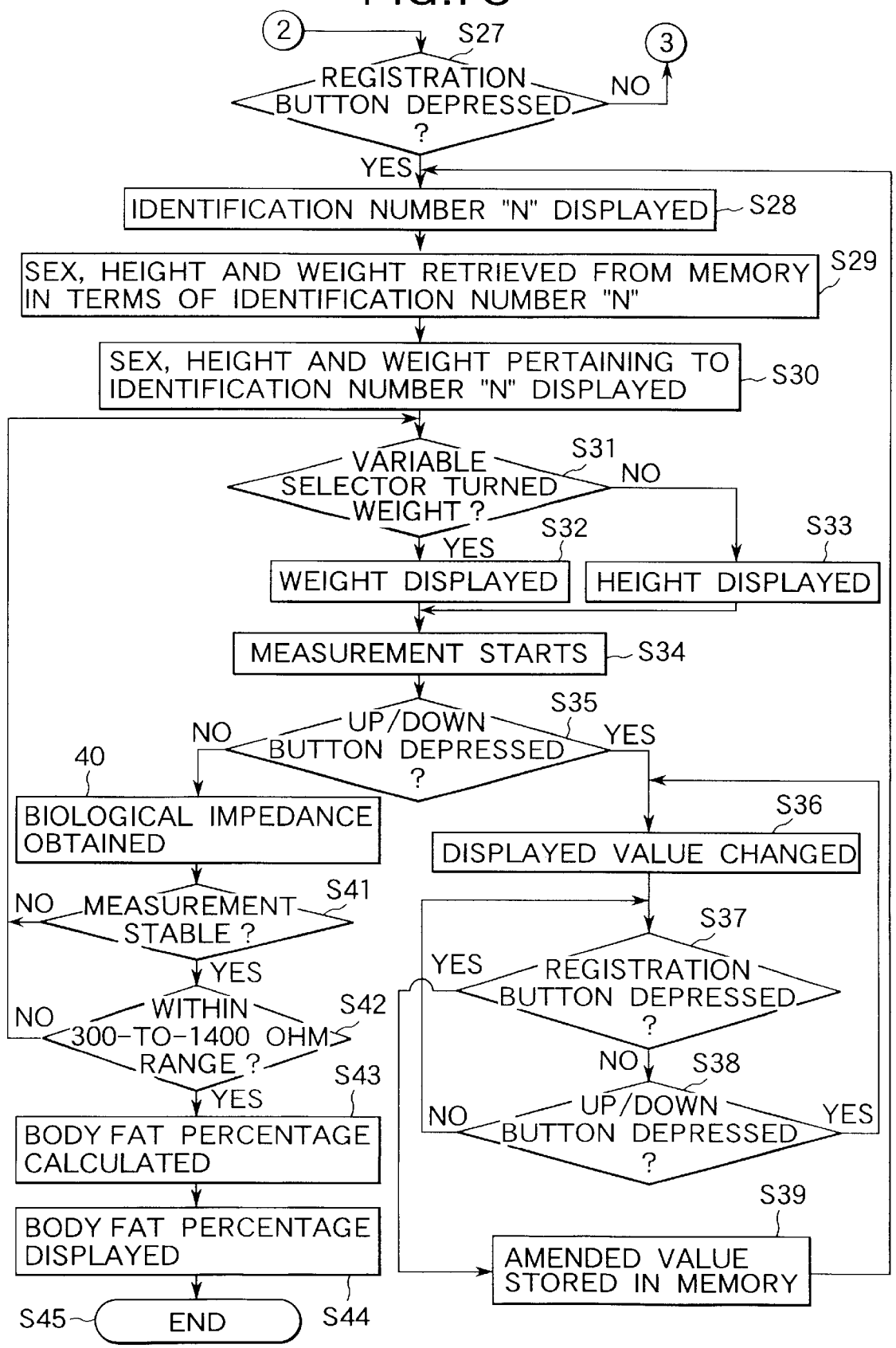
Figure 8A:
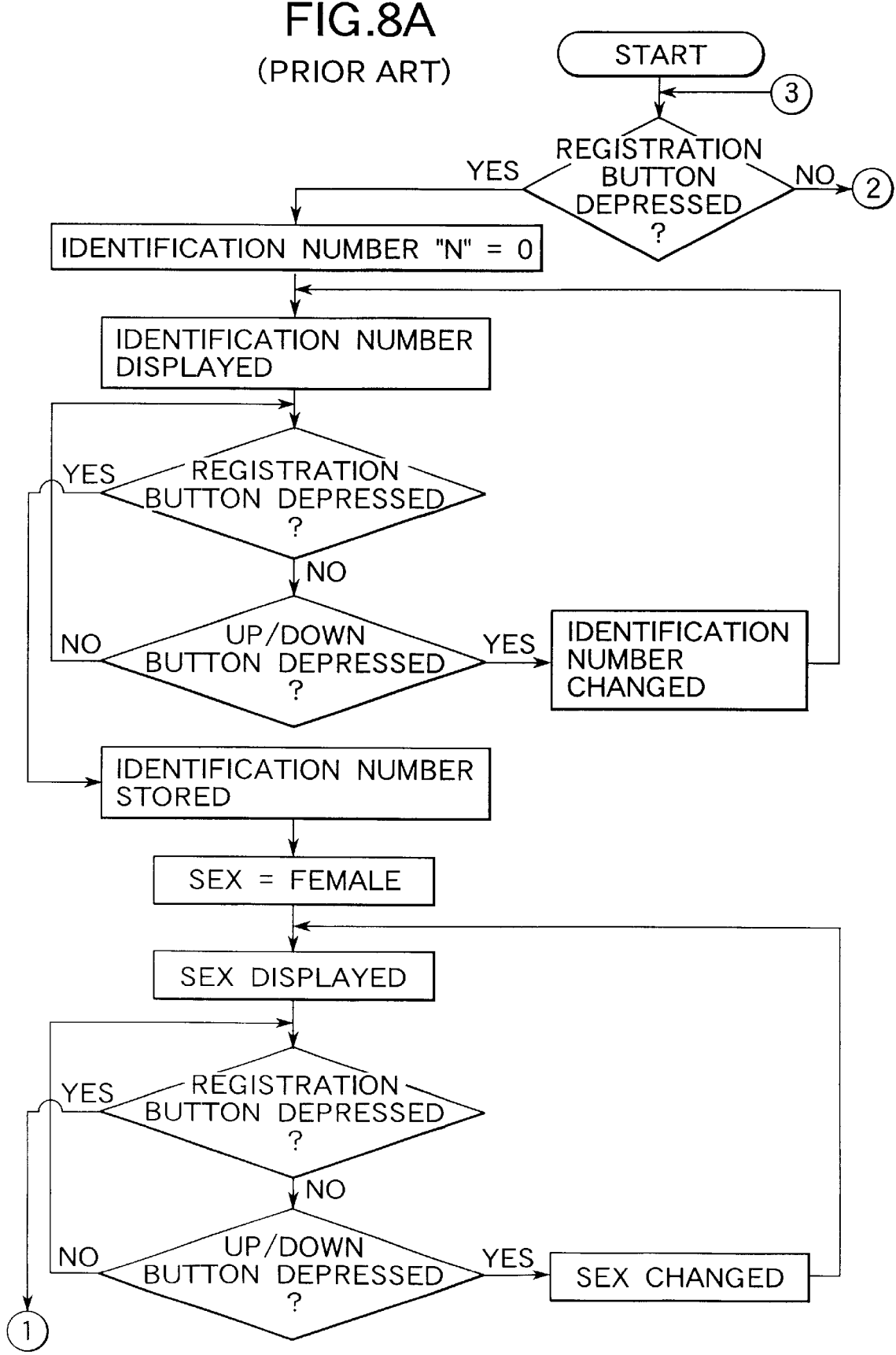
Figure 8B:
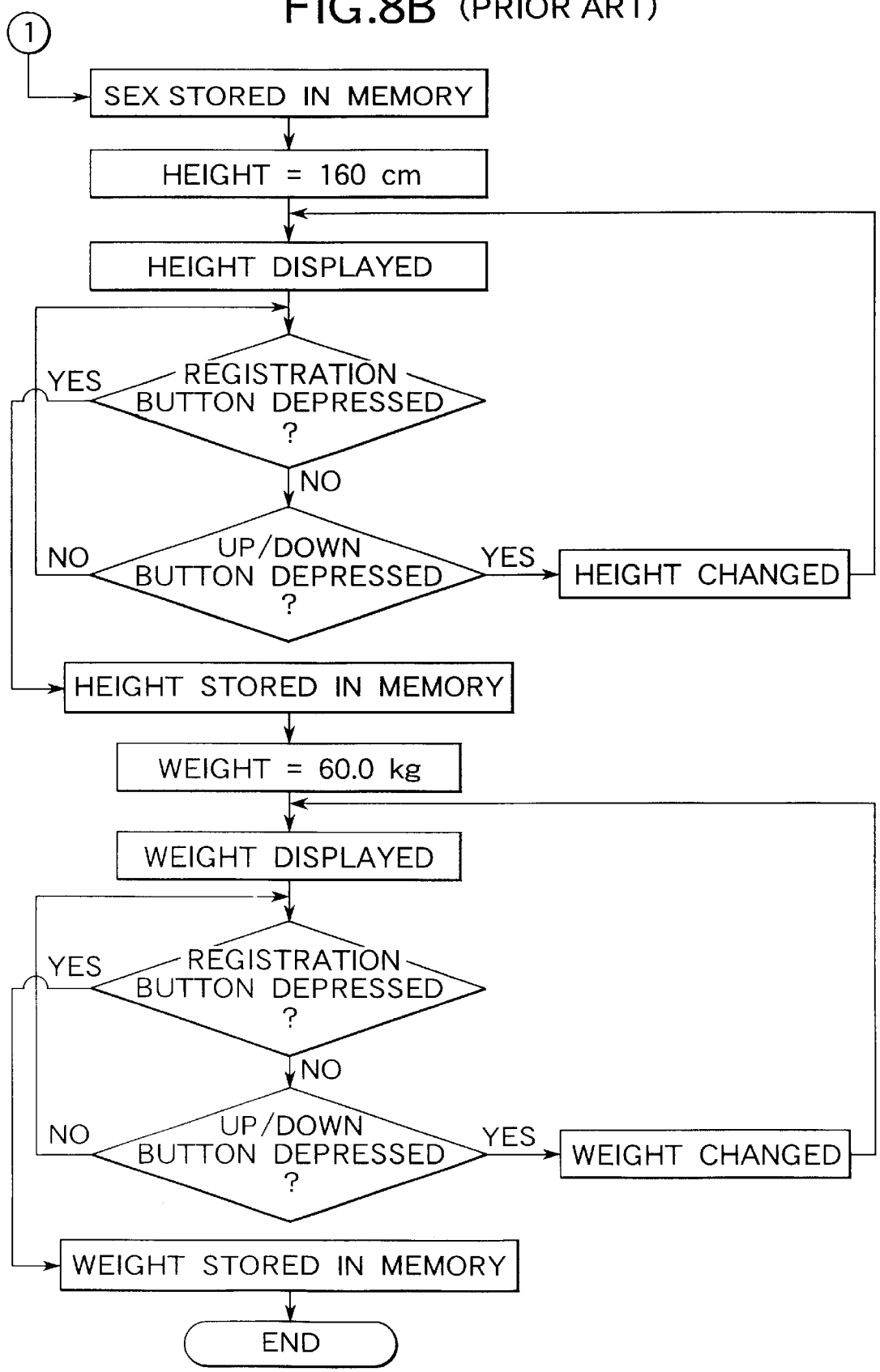

Referring to FIGS. 7A, 7B and 7C, a series of actions taken by the body fat percentage gauge when being set up appear in FIGS. 7A and 7B, and are same as in FIGS. 3A and 3B. The description of the "set up" actions is omitted. As described above, all pieces of physical information pertaining to the individual are registered, and the individual data setting mode is finished. Then, another series of actions taken by the gauge when measuring the body fat percentage (see FIG. 7C) start.

If the registration push button 6 is not depressed at Step S1, a check is made as to whether or not either push button for measurement 5A or 5B has been depressed (Step S27). In the negative case the proceeding returns to Step S1. The body fat percentage gauge remains dormant until either measurement push button 5A or 5B has been depressed. Contrary, if the registration push button 6 is found to have been depressed at Step S27, the identification number "n" pertaining to the depressed measurement push button is allowed to appear in the display 4 (Step S28), so that the sex, the height and the weight of the individual thus identified in terms of identification number "n" are retrieved from the memory (Step S29). The so retrieved sex, height and weight are allowed to appear one after another in the display 4 (Step S30). Here, it is checked on which side the variable selector switch 9 is shifted, "W" or "H" (Step S31). If it is shifted to "W", the display 4 continues to show the weight (Step S32). Contrary if it is shifted to "H", the display 4 continues to show the height (Step S33). Then, the body fat rate gauge 1 is put in the measurement-permitting condition, allowing the display 4 to continue to show the piece of physical information selected at Step S31. This continuous display informs the user of the permissibility of changing the displayed value on demand (Step S34).

Here, a check is made as to whether or not either scroll push button 7 or 8 has been depressed (Step S35). In the affirmative case the amended value is shown in the display 4 (Step S36). A check is made as to whether or not the registration push button 6 has been depressed (Step S37). Thus, the user is being asked whether the amended and displayed value can be registered. In the negative case a check is made as to whether or not either scroll push button 7 or 8 has been depressed (Step S38). If either scroll push button 7 or 8 is depressed, the proceeding is allowed to return to Step S36 for renewal of the displayed value. Otherwise, the proceeding is allowed to return to Step S37 to confirm that the present value should be registered. Depression of the registration push button 6 at Step 37 allows the memory to store the amended value, and then the preceding returns to Step S28 (Step S39).

If either scroll push button 7 or 8 is not depressed for renewal of values at Step 35, a biological impedance is calculated (Step S40). The calculation is repeated several times within a relatively short time, and a check is made as to whether or not the so determined values of biological impedance remain within a certain range (Step S41). If the so determined values of biological impedance are found to be unstable, increasing or decreasing beyond the certain range, the proceeding returns to Step S31 where which side the switch 9 is turned is checked. When the so determined values of biological impedance are found to be stable, it is checked whether these values remain within the range from 300 to 1,400 Ω (Step S42). The values of biological impedance appearing between both hands of children and adults remain in the range from 300 to 1,400 Ω. If the measurement is effected with both hand skins touched on the electrodes, the values of biological impedance must remain within the range. Stated otherwise, if the values of biological impedance are found to be out of the range, either hand skin is supposed to have been untouched rightly on the electrodes on which it must be put.

As described earlier, the user uses his thumbs in changing some pieces of physical information already registered, and then, he must take at least one of both thumbs off from the voltage measuring electrode, resulting in the value of biological impedance departing apart from the prescribed range. Continuous measurement of biological impedance reveals that the user is changing the registered value of his weight, and then, the display device continues to show the registered value of weight. Thus, the user can compare the present weight with the registered one until the value of biological impedance has been stable in measurement. When the measured value of biological impedance is found to be stable at Step S41, and when the measured value is found to remain within the 300-to-1400 ohm range at Step S42, the user is supposed to put his fingers on the electrodes, indicating his desire for measurement of biological impedance. Thus, some words, such as "measurement continued" appear in the display 4.

The body fat percentage is calculated from the measured value of biological impedance and some pieces of physical information retrieved from the memory, such as the sex, the height and the (amended) weight (Step S43). The body fat percentage thus calculated is shown in the display 4 (Step S44), and it will disappear from the display 4 in a given length of time, thus completing all measurements (Step S45).

The biological impedance appearing between both hands is described as remaining in the range from 300 to 1400 Ω, but such range should not be understood to be limitative.

The body fat percentage determined from the biological impedance and some pieces of physical information as described above is the rate of the fat volume to the whole volume of the individual body. The body fat percentage may be given in terms of percentage by weight.

Some push switch buttons 5 to 8 are used to perform different functions allotted thereto, but cross-shaped switches may be used without substantially altering the circuit structure of the body fat percentage gauge.

The body fat percentage gauge is described as permitting pieces of physical information to be registered for two persons. Specifically it has two push buttons for measurement allotted to two persons. Of course, the number of the push buttons for measurement can be three or more.

The variable selector switch 9 is described as being capable of making a selection between two pieces of physical information, that is, height and weight. This should not be understood as limitative, and a desired selection can be made among three or more pieces of information.

The present invention is described as being applied to a hand-held type of body fat percentage gauge, but it can be equally applied to a weight scale-like body fat percentage gauge, which is so designed as to measure the body fat percentage from the biological impedance appearing between both feet. While a user is changing a selected piece of physical information already registered, he must change his posture, as for instance follows: he crouches down or sits down to handle the console or he raise the whole gauge up. In any event his feet are taken away or displaced from the electrodes on the weight scale-like object, thus causing the value of biological impedance to be unstable. Such unstable condition can be detected as being indicative of the user's changing some selected variables such as age or height stored in the memory if the weight scale type of body fat percentage gauge is modified according to the present invention.

Apparatuses for measuring blood pressure, pulsation or heartbeat as indicative of health include sensors to be applied to individual bodies for measurement. Such and other apparatuses performing required measurements by applying their sensors to the skin of the individual can be so modified according to the present invention that the unstable condition may be detected as being indicative of the user's changing some selected variables, and that some selected pieces of physical information may be changed exclusively with ease.

The object whose characteristic value is measured need not be limited to human beings. In measuring some characteristics of a non-living object a decision as to whether or not the measurement is continued can be made from appearance of unusual values of such characteristics according to the present invention. Thus, the present invention can be applied to not only the health indicators but also a variety of measuring apparatuses.

As may be understood from the above, a measuring apparatus according to the present invention facilitates the changing of any selected pieces of information already registered in the memory without the necessity of repeating the recording of the other registered pieces of information. Accordingly the operability of the measuring apparatus is improved.

A health indicator to which the present invention is applied facilitates renewal of any pieces of physical information without the necessity of repeating the recording of the other registered pieces of physical information. Exclusive renewal of selected variables, which are registered in the memory, and are often required to be renewed, is permitted, and accordingly the operability of the gauge is improved.

Specifically a body fat percentage measuring apparatus to which the present invention is applied permits exclusive renewal of weight without the necessity of repeating the recording of the other registered pieces of unchangeable or least changeable information, such as sex or age. This faculty provides a significant convenience in dieting or physically training; one's weight is likely to vary almost every day.

Different pieces of information which are supposed to be often required for renewal are selected beforehand among those registered in the memory, and one of the so selected variables can be selected for renewal to meet the demand while the gauge is put in condition for measurement. This improves the operability of the gauge in case that two or more variables are equally often changeable and that only one variable is required for renewal for each measurement.

What is claimed is:

1. A measuring apparatus comprising: an inputting device comprising;

an inputting-and-setting switch for inputting and recording a plurality of pieces of information, data-modifying switches for changing a selected one or ones of the plurality of pieces of information and a measurement starting switch for starting measurement of a certain characteristic of an object;

a measuring device for measuring the certain characteristic of the object;

a memory device for storing the plurality of pieces of information inputted by the inputting device;

an arithmetic and control unit (ACU) for determining a required indicia from the certain characteristic of the object and from the plurality of pieces of information; and a display for showing the plurality of pieces of information and the so determined indicia, characterized in that the arithmetic and control unit is responsive to depression of the data-modifying switches on condition that there is no depression of the imputting-and-setting switch subsequent to depression of the measurement starting switch for putting the measuring apparatus in its inputting state, thereby permitting alteration of only a selected variable one of the plurality of pieces of information.

2. A measuring apparatus according to claim 1 wherein it comprises a selector switch for selecting a desired piece of information for alteration among the selected ones of the plurality of pieces of information.

3. A measuring apparatus according to claim 2 wherein the arithmetic and control unit is responsive to depression of the measurement starting switch for permitting the display device to show a registered piece of information for alteration in the display prior to and during the measurement of the certain characteristic of the object.

4. A measuring apparatus according to claim 3 wherein the arithmetic and control unit is responsive to appearance of unusual values as representing the certain characteristic of the object for permitting the display device to continue to show the registered piece of information for alteration, for repeating determination of the certain characteristic of the object until the so determined characteristic of the object has been reduced to a normal value, and for obtaining the indicia from the normal value of the characteristic of the object finally determined and selected pieces of information retrieved from the memory, thereby permitting the display to show the required indicia.

5. A healthy indicia measuring apparatus comprising:

an inputting device comprising an inputting-and-setting switch for inputting and recording a plurality of pieces of physical information pertaining to each individual, data-modifying switches for changing a selected one or ones of the plurality of pieces of physical information and a measurement starting switch for starting measurement of a certain characteristic of each individual;

sensors for obtaining a selected piece or pieces of biological information;

a memory for storing the plurality of pieces of physical information pertaining to each individual inputted by the inputting device;

an arithmetic and control unit (ACU) for determining a healthy indicia from the stored pieces of physical information and from the measured piece of biological information; and a display for showing the pieces of physical information and the so determined healthy indicia, characterized in that the arithmetic and control unit is responsive to depression of the data-modifying switches on condition that there is no depression of the imputting-and-setting switch subsequent to depression of the measurement starting switch for putting the measuring apparatus in its inputting state, thereby permitting alteration of only a selected variable one of the plurality of pieces of information.

6. A healthy indicia measuring apparatus according to claim 5 wherein it further comprises a selector switch for selecting a desired piece of information among two or more selected ones of the stored pieces of physical information.

7. A healthy indicia measuring apparatus according to claim 5 wherein the arithmetic and control unit is responsive to depression of the measurement starting switch for permitting the display device to show a given piece of physical information for alteration in the display prior to and during the measurement of the biological information.

8. A healthy indicia measuring apparatus according to claim 7 wherein the arithmetic and control unit may be responsive to appearance of unusual values as representing the measurement of the piece of biological information for permitting the display device to continue to show the registered piece of physical information for alteration, for repeating determination of the biological information of the individual until the so determined biological information has been reduced to a normal value, and for obtaining the healthy indicia from the normal value of the so determined biological information and selected pieces of physical information retrieved from the memory, thus permitting the display to show the required healthy indicia.

9. A body fat percentage measuring apparatus comprising:

an inputting device comprising an inputting-and-setting switch for inputting device comprising an inputting-and-setting switch for inputting and recording a plurality of pieces of physical information for pertaining to each individual, data-modifying switches for changing the sex, the age, the height, the weight and other pieces of physical information of each individual, and a measurement starting switch for starting the measurement of the body fat percentage for each individual;

a biological impedance sensor having electrodes to be applied to the individual body;

a memory for storing the pieces of physical information pertaining to each individual inputted by the inputting device;

an arithmetic and control unit (ACU) for determining the body fat percentage from the determined biological impedance and from the stored pieces of physical information; and a display for showing the pieces of physical information and the so determined body fat percentage, characterized in that the arithmetic and control unit is responsive to depression of the data-modifying switches on condition that there is no depression of the imputting-and-setting switch subsequent to depression of the measurement starting switch for putting the measuring apparatus in its inputting state, thereby permitting alteration of only a selected variable one of the plurality of pieces of information pertaining to each individual.

10. A body fat percentage measuring apparatus according to claim 9 wherein it further comprises a selector switch for selecting a desired piece of information among two or more selected ones of the pieces of physical information.

11. A body fat percentage measuring apparatus according to claim 9 wherein the arithmetic and control unit is responsive to depression of the measurement starting switch for permitting the display device to show the registered piece of physical information for alteration in the display prior to and during the measurement of the biological impedance.

12. A body fat percentage measuring apparatus according to claim 11 wherein the arithmetic and control unit is responsive to appearance of unusual values as representing the biological impedance for permitting the display device to continue to show the registered piece of information desired for alteration, for repeating determination of the biological impedance until the so determined biological impedance has been reduced to a normal value, and for obtaining the body fat percentage from the normal value of the biological impedance and selected pieces of information retrieved from the memory, thus permitting the display to show the required body fat percentage.

13. A body fat percentage measuring apparatus according to claim 9 wherein one piece of physical information to be selected for alteration is weight.

14. A body fat percentage measuring apparatus according to claim 10 wherein the piece of physical information selected for alteration is one of the weight and height selected by the selector switch.

* * * * *